(12) United States Patent
Treado et al.

(10) Patent No.: US 8,368,880 B2
(45) Date of Patent: Feb. 5, 2013

(54) CHEMICAL IMAGING EXPLOSIVES (CHIMED) OPTICAL SENSOR USING SWIR

(75) Inventors: Patrick Treado, Pittsburgh, PA (US); Matthew Nelson, Harrison City, PA (US); Charles W. Gardner, Jr., Gibsonia, PA (US)

(73) Assignee: ChemImage Corporation, Pittsburgh, PA (US)

(*) Notice: Subject to any disclaimer, the term of this patent is extended or adjusted under 35 U.S.C. 154(b) by 367 days.

(21) Appl. No.: 12/754,229

(22) Filed: Apr. 5, 2010

(65) Prior Publication Data

US 2010/0225899 A1   Sep. 9, 2010

Related U.S. Application Data

(63) Continuation-in-part of application No. 11/645,132, filed on Dec. 22, 2006, now Pat. No. 7,692,776.

(60) Provisional application No. 60/754,011, filed on Dec. 23, 2005, provisional application No. 61/305,667, filed on Feb. 18, 2010, provisional application No. 61/335,785, filed on Jan. 12, 2010, provisional application No. 61/301,814, filed on Feb. 5, 2010.

(51) Int. Cl.
G01N 21/00 (2006.01)

(52) U.S. Cl. ...................................................... 356/73

(58) Field of Classification Search ............. 356/72–73; 250/338.1, 339.11, 341.8
See application file for complete search history.

(56) References Cited

U.S. PATENT DOCUMENTS

| | | | |
|---|---|---|---|
| 5,606,164 A | 2/1997 | Price et al. | |
| 6,075,891 A | 6/2000 | Burman | |
| 6,421,553 B1 | 7/2002 | Costa et al. | |
| 6,967,612 B1 | 11/2005 | Gorman | |
| 6,985,216 B2 | 1/2006 | Treado et al. | |
| 6,992,809 B1 | 1/2006 | Wang | |
| 7,012,695 B2 | 3/2006 | Maier et al. | |
| 7,019,296 B2 | 3/2006 | Treado et al. | |
| 7,061,606 B2 | 6/2006 | Treado et al. | |
| 7,068,357 B2 | 6/2006 | Treado et al. | |
| 7,072,770 B1 | 7/2006 | Schweitzer et al. | |
| 7,123,360 B2 | 10/2006 | Treado et al. | |
| 7,268,861 B2 | 9/2007 | Treado et al. | |
| 7,268,862 B2 | 9/2007 | Treado et al. | |
| 7,277,178 B2 | 10/2007 | Shpantzer | |
| RE39,977 E | 1/2008 | Treado et al. | |
| 7,317,516 B2 | 1/2008 | Treado et al. | |
| 7,322,267 B1 | 1/2008 | Munson | |

(Continued)

FOREIGN PATENT DOCUMENTS

EP  2083259  7/2009
WO  PCT/US05/25112  2/2006

(Continued)

OTHER PUBLICATIONS

Williams et al., "Multicamera-multispectral video library—an algorithm development tool", Applied Imagery Pattern Recognition Workshop, 2008, pp. 1-5.*

(Continued)

*Primary Examiner* — Kara E Geisel

(57) ABSTRACT

A sample is illuminated to thereby generate a plurality of first interacted photons selected. The first interacted photons are assessed using a visible imaging device to thereby determine an area of interest in the sample. The area of interest is illuminated to thereby generate a plurality of second interacted photons. The second interacted photons are assessed using a spectroscopic device to thereby generate a SWIR data set representative of said area of interest. A database is searched wherein said database comprises a plurality of known SWIR data sets associated with an explosive material. The data sets comprise at least one of: a plurality of SWIR spectra and a plurality of spatially accurate wavelength resolved SWIR images. An explosive material in the area of interest is thereby identified as a result of the search.

18 Claims, 10 Drawing Sheets

U.S. PATENT DOCUMENTS

| | | | |
|---|---|---|---|
| 7,362,489 | B2 | 4/2008 | Wang |
| 7,362,839 | B2 | 4/2008 | Goth |
| 7,409,299 | B2 | 8/2008 | Schweitzer et al. |
| 7,417,727 | B2 | 8/2008 | Polonskiy |
| 7,417,796 | B2 | 8/2008 | Wang |
| 7,420,664 | B2 | 9/2008 | Treado |
| 7,420,675 | B2 | 9/2008 | Giakos |
| 7,436,500 | B2 | 10/2008 | Treado et al. |
| 7,479,966 | B2 | 1/2009 | Maier et al. |
| 7,502,188 | B2 | 3/2009 | Inomata |
| 7,511,624 | B2 | 3/2009 | Shaw |
| 7,525,102 | B1 | 4/2009 | Henshaw |
| 7,551,715 | B2 | 6/2009 | Rothschild |
| 7,679,740 | B2 | 3/2010 | Neiss et al. |
| 7,705,981 | B2 | 4/2010 | Maier et al. |
| 2003/0085348 | A1 | 5/2003 | Megerle |
| 2003/0123056 | A1 | 7/2003 | Barnes |
| 2004/0051867 | A1 | 3/2004 | Brestel et al. |
| 2005/0105099 | A1 | 5/2005 | Shpantzer |
| 2005/0137806 | A1 | 6/2005 | Kutsyy et al. |
| 2005/0264813 | A1 | 12/2005 | Giakos |
| 2006/0077377 | A1 | 4/2006 | Brestel et al. |
| 2006/0100524 | A1 | 5/2006 | Lucassen et al. |
| 2006/0203238 | A1 | 9/2006 | Gardner et al. |
| 2006/0219937 | A1 | 10/2006 | Henry et al. |
| 2006/0254522 | A1 | 11/2006 | Shaw |
| 2007/0007384 | A1 | 1/2007 | Sliwa |
| 2007/0098142 | A1 | 5/2007 | Rothschild |
| 2007/0125951 | A1 | 6/2007 | Snider |
| 2007/0127030 | A1 | 6/2007 | Shpantzer |
| 2007/0139772 | A1 | 6/2007 | Wang |
| 2007/0166045 | A1 | 7/2007 | Wang |
| 2007/0192035 | A1 | 8/2007 | Schweitzer et al. |
| 2007/0268485 | A1 | 11/2007 | Polonskiy |
| 2008/0036593 | A1 | 2/2008 | Rose-Pehrsson |
| 2008/0062353 | A1 | 3/2008 | Wang |
| 2008/0084553 | A1 | 4/2008 | Neiss et al. |
| 2008/0084564 | A1* | 4/2008 | He et al. ............ 356/456 |
| 2008/0129581 | A1 | 6/2008 | Douglass |
| 2008/0144885 | A1 | 6/2008 | Zucherman |
| 2008/0165344 | A1 | 7/2008 | Treado et al. |
| 2008/0191137 | A1 | 8/2008 | Poteet |
| 2008/0192246 | A1 | 8/2008 | Neiss et al. |
| 2008/0198365 | A1 | 8/2008 | Treado |
| 2008/0204757 | A1 | 8/2008 | Manning |
| 2008/0258071 | A1 | 10/2008 | Arnold |
| 2008/0268548 | A1 | 10/2008 | Zuckerman |
| 2008/0291426 | A1* | 11/2008 | Azimi et al. ............ 356/73 |
| 2008/0295783 | A1 | 12/2008 | Furton |
| 2008/0300826 | A1 | 12/2008 | Schweitzer et al. |
| 2009/0012723 | A1 | 1/2009 | Treado et al. |
| 2009/0021730 | A1 | 1/2009 | Maier et al. |
| 2009/0043514 | A1 | 2/2009 | Schweitzer et al. |
| 2009/0046393 | A1 | 2/2009 | Davey |
| 2009/0066947 | A1 | 3/2009 | Bangalore et al. |
| 2009/0095885 | A1 | 4/2009 | Hager |
| 2009/0101843 | A1 | 4/2009 | Henshaw |
| 2009/0128802 | A1 | 5/2009 | Treado et al. |
| 2009/0236528 | A1 | 9/2009 | Shpantzer |
| 2009/0252650 | A1 | 10/2009 | Lakshmanan |
| 2009/0257555 | A1 | 10/2009 | Chalmers |
| 2010/0051809 | A1 | 3/2010 | Onat et al. |

FOREIGN PATENT DOCUMENTS

| | | |
|---|---|---|
| WO | PCT/IB2006/052448 | 1/2007 |
| WO | PCT/US2005/036593 | 1/2007 |
| WO | PCT/US2006/027172 | 3/2007 |
| WO | PCT/US2006/060158 | 3/2007 |
| WO | PCT/US2005/033740 | 4/2007 |
| WO | PCT/US2006/012300 | 4/2007 |
| WO | PCT/US2006/060683 | 5/2007 |
| WO | PCT/US2005/044648 | 7/2007 |
| WO | PCT/US2007/015132 | 3/2008 |
| WO | PCT/US2007/018347 | 4/2008 |
| WO | PCT/US2007/081551 | 4/2008 |
| WO | PCT/US2007/016040 | 8/2008 |

OTHER PUBLICATIONS

Onat, Bora M. et al., A Solid State Hyperspectral Imager for Real-Time Standoff Explosives Detection Using Shortwave Infrared Imaging, Proc. of SPIE vol. 7310, 731004-1 to 731004-11.

Sharma, S.K. et al., Combined Remote LIBS and Raman Spectroscopy of Minerals Using a Single Laser Source, Lunar Planet Sci. XXXVIII, 2007.

Clegg, S.M. et al., LIBS-Raman Spectroscopy of Minerals Using Remote Surface Modification Techniques, Mar. 2006, Lunar Planet Sci. XXXVII, 2006.

Thompson, J. et al., Combined Remote LIBS and Raman Spectroscopy Measurements, Lunar Planet Sci, XXXVI, 2005.

Weins, R.C., Development of a Prototype Laser-Induced Breakdown Spectroscopy (LIBS) Instrument and Stand-off Raman Capabilities as Part of the Mars Instrument Development Program, Lunar Planet Sci., XXXI.

Poster-Session: Mars Polar Science, Astrobiology, Future Missions/Instruments and Other Mars Science, Jul. 2007, Secenth International Conference on Mars, Session 11.

Marquardt, Brian J. et al., Novel Probe for Laser-Induced Breakdown Spectroscopy and Raman Measurements Using an Imaging Optical Fiber (Jun. 1998) vol. 52, No. 9.

U.S. Appl. No. 12/430,581 (not yet published), Apr. 2009.
U.S. Appl. No. 11/544,727 (not yet published), Oct. 2006.
U.S. Appl. No. 12/504,914 (not yet published), Jul. 2009.
U.S. Appl. No. 12/441,420 (not yet published), Jul. 2010.
Office Action, U.S. Appl. No. 11/632,471, Feb. 17, 2008.
Office Action, U.S. Appl. No. 11/632,471, Apr. 12, 2009.
Office Action, U.S. Appl. No. 11/632,471, Apr. 16, 2008.
Office Action, U.S. Appl. No. 11/645,132, Apr. 1, 2009.
PCT/US06/49176, Search Report, Mar. 6, 2008, and written opinion.

* cited by examiner

RGB Image        AN Fingerprint Detection Image

CHEMICAL IMAGING EXPLOSIVES (CHIMED) OPTICAL SENSOR USING SWIR

RELATED APPLICATIONS

This application is a continuation-in-part of U.S. patent application Ser. No. 11/645,132, filed on Dec. 22, 2006, entitled "Chemical Imaging Explosives Optical (CHIMED) Sensor", which in turn claims priority to U.S. Provisional Application No. 60/754,011, filed on Dec. 23, 2005, entitled "Chemical Imaging Explosives Optical (CHIMED) Sensor." This application also claims priority to U.S. Provisional Application No. 61/305,667, filed on Feb. 18, 2010, entitled "System and Method for Detecting Explosives on Shoes and Clothing", U.S. Provisional Application No. 61/335,785, filed on Jan. 12, 2010, entitled "System and Method for SWIR HSI for Daytime and Nighttime Operations", and U.S. Provisional Application No. 61/301,814, filed on Feb. 5, 2010, entitled "System and Method for Detecting Hazardous Agents Including Explosives." These applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can he implemented by one of two methods. First, a point-source illumination can he provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR) wavelengths and to some overlapping ranges. These correspond to wavelengths of about 180-380 nm (UV), 380-700 nm (VIS), 700-2500 nm (NIR), 900-1700 nm (SWIR), and 2500-25000 nm (MIR).

There currently exists a need for accurate detection of explosives and explosive residues. In particular, there exists a need for a system and method for the accurate detection of explosives and explosive residues associated with transportation passengers and other individuals at security checkpoints, points of inspection and other similar locations. There also exists a need for a system and method for the detection of such materials located in or on a person or an article associated with that person, including clothing items.

FIELD OF DISCLOSURE

The present disclosure relates generally to a system and method for the detection of explosive materials and residues using spectroscopic methods. More specifically, the present disclosure relates to the use of visible (RGB) and short wave infrared ("SWIR") hyperspectral imaging to detect explosive materials.

SUMMARY

The system and method of the present disclosure provide for a Chemical Imaging Explosive Detector ("CHIMED Sensor") to address the current need for detection of explosive materials. The present disclosure provides for a system and method for the detection of explosive materials using visible imaging and short-wave infrared (SWIR) spectroscopic methods. The system and method disclosed herein hold potential for a variety of applications including the detection of explosives and explosive residue on an individual such as a transportation passenger at a security checkpoint. The present disclosure contemplates the use of hyperspectral imaging technology to detect and identify chemical, biological, and explosive compounds in non-contact, reagentless configurations. The present disclosure contemplates the application of the system and method described herein in proximity, stand-off, and On-the-Move (OTM) configurations.

The present disclosure provides for a system and method of detecting explosive materials, including explosive residues. These explosive materials may be present on or in a sample of interest. The sample may include, but is not limited to, items such as a human hand, a passport, a credit card, a driver's license, a boarding pass, a human body part, a piece of human clothing, a human-wearable item, shoes, an airline ticket, and other items that may have come in contact with a human being. Additionally, the sample may be present in a region of interest of either an indoor or outdoor scene. The technology described herein may be used to detect Improvised Explosive Devices (IEDs), emplacements (such as DE and aged concrete), command wires, EFP wires, EFP camouflage, and explosive residue, among other materials including but not limited to those associated with explosive compounds and concealments.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

Figure 1A:
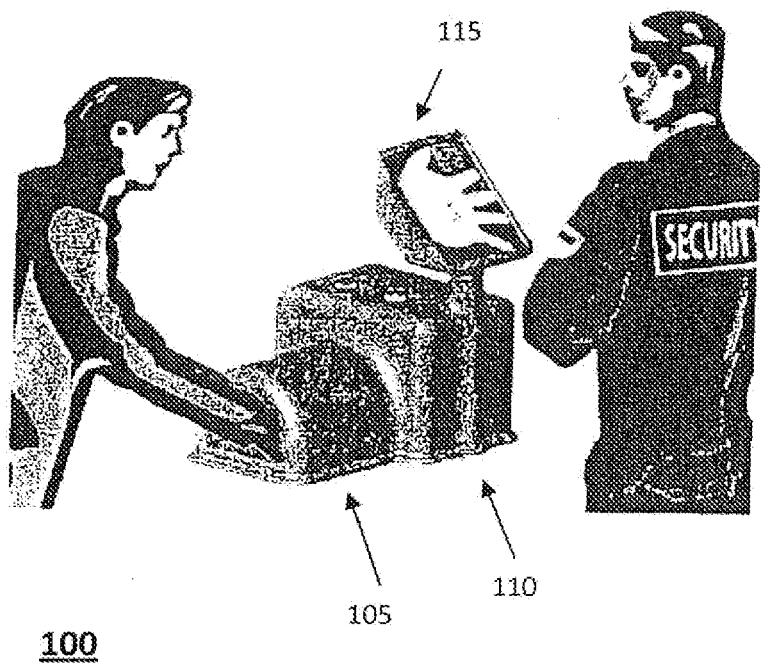
FIGS. 1A and 1B illustrate schematic representations of exemplary embodiments of the sensor system of the present disclosure.
Figure 1B:
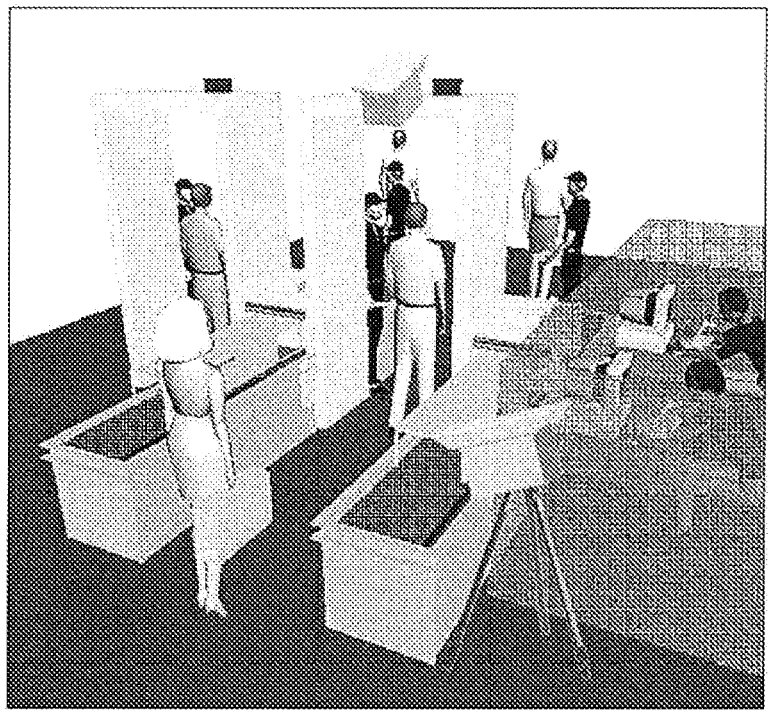

FIG. 1A illustrates an exemplary sensor system of the present disclosure. Sensor system 100 includes a sample chamber 105, a monitoring device 110 and a viewing screen 115. FIG. 1B is illustrative of another embodiment of the present disclosure. In such an embodiment, transportation passengers are sequentially or consecutively screened for explosive materials while passing though a security checkpoint. Such an embodiment may apply the standoff and OTM configurations discussed herein.

Figure 2:
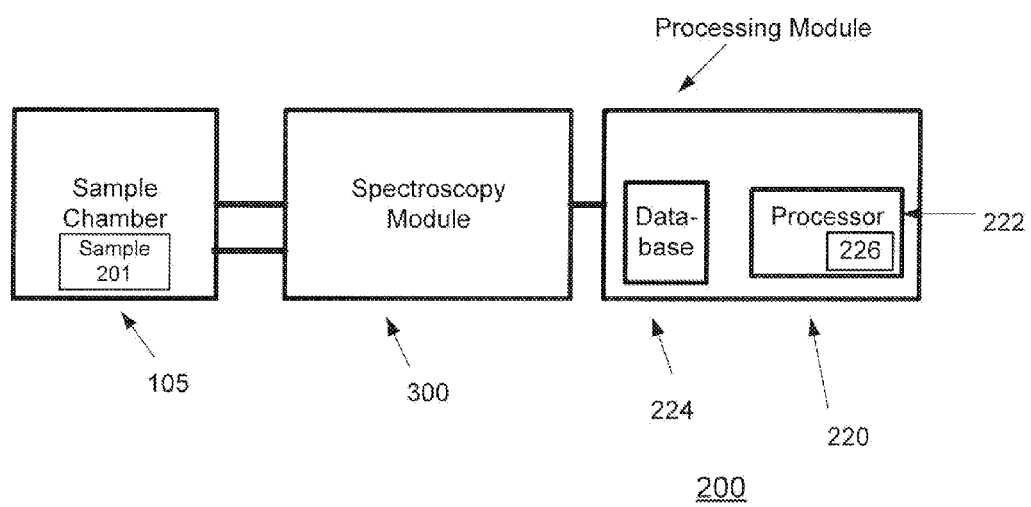
FIG. 2 illustrates a schematic representation of another exemplary sensor system of the present disclosure.

FIG. 2 illustrates a second exemplary system 200 of the present disclosure. Sensor system 200 includes sample chamber 105, spectroscopy module 200 and processing module 220. Sample 201 is placed inside sample chamber 105 for analysis. Processing module 220 includes processor 222, database 224, and machine readable program code 226. Spectroscopy module 200 may include a plurality of detectors in one embodiment of the present disclosure. The detectors may include a digital device such as an image focal plane array ("FPA") or CCD or CMOS sensor. The optical region employed to characterize the sample of interest governs the choice of a two-dimensional array detector. In other embodiments, gallium arsenide (GaAs) and Gallium indium arsenide (GaInAs) FPA detectors can be employed for image analysis. The choice of such devices. depends on the type of sample being analyzed. The machine readable program code 228 contains executable program instructions. Processor 222 is configured to execute the machine readable program code 226 so as to perform the methods of the present disclosure.

Referring again to FIG. 2, SWIR data sets may be stored in the database 244 of processing module 220. In another embodiment, the processing module 220 may comprise at least one additional database. Such a database may comprise visible data sets. In another embodiment, database 224 includes at least one of a plurality of known visible data sets and a plurality of known SWIR data sets. In one embodiment, the plurality of known visible data sets may comprise visible images including RGB and brightfield images. In one embodiment, the plurality of SWIR data sets may comprise at least one of a plurality of SWIR spectra and a plurality of spatially accurate wavelength resolved SWIR images.

Each known visible data set and each SWIR data set may be associated with a known compound. In one embodiment, the known compounds include suspicious chemical substances such as explosive compounds, a residue of an explosive compound, a formulation additive of explosive material, a binder of explosive material, a biohazard or an illegal drug. Representative known explosive compounds may include but are not limited to: nitrocellulose, Ammonium nitrate ("AN"), nitroglycerin, 1,3,5-trinitroperhydro-1,3,5-triazine ("RDX"), 1,3,5,7tetranitroperhydro-2,3,5,7-tetrazocine ("HMX") and 1,3,-Dinitrato-2,2-bis (nitratomethyl) propane ("PETN").

In one embodiment, processor 222 may be configured to execute a machine readable program code 226 to search database 224. The database 224 can be searched using a variety of similarity metrics. In one embodiment, the similarity metric produces a score. Representative metrics include principal component analysis (PCA), multivariate curve resolution (MCR), cosine correlation analysis (CCA), Euclidian distance analysis (EDA), partial least squares regression (PLSR), or spectral mixture resolution (SMR), a spectral angle mapper metric, a spectral information divergence metric, a Mahalanobis distance metric and a spectral unmixing algorithm. A spectral unmixing metric is disclosed in U.S. Pat. No. 7,072,770 entitled "Method for Identifying Components of a Mixture via Spectral Analysis," which is hereby incorporated by reference in its entirety.

In one embodiment, the present disclosure provides for irradiating a sample with animal-safe ultra-violet radiation to thereby generate a fluorescence data set representative of said sample. A fluorescence database is then searched based on the fluorescence data set in order to identify a known fluorescence data set. If the searching identifies a known fluorescence data set, an area of interest in the sample is identified based on the known fluorescence data set identified in the fluorescence database searching. The area of interest is irradiated with substantially monochromatic radiation to generate a Raman data set of the area of interest. A Raman database is searched based on the Raman data set. An explosive compound in the area of interest is identified based on the known Raman data set identified by searching the Raman database. This is embodiment is more fully described in U.S. patent application Ser. No. 11/645,132, entitled "Chemical Imaging Explosives (CHIMED) Optical Sensor", filed on Dec. 22, 2006, which is hereby incorporated by reference in its entirety.

Figure 3:
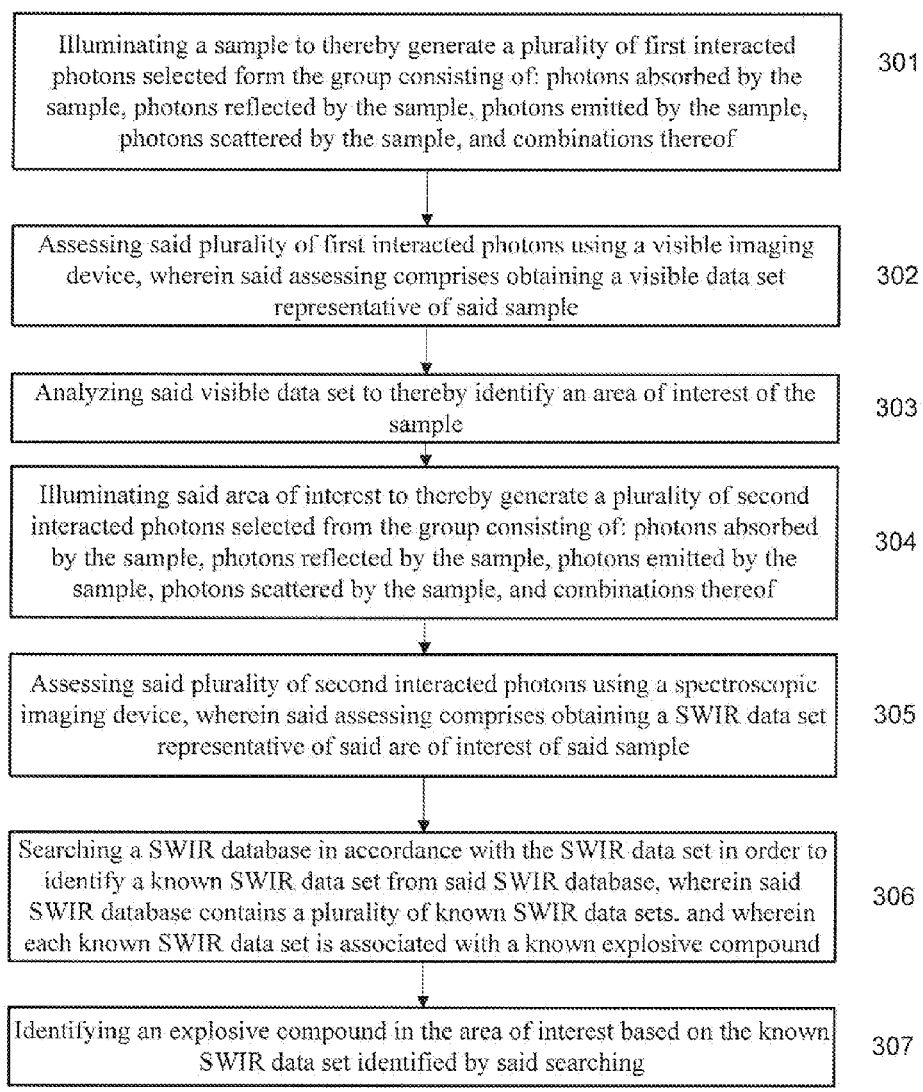
FIG. 3 is representative of a method of the present disclosure.

FIG. 3 is a flowchart illustrative of a method of the present disclosure. The method 300 provides for illuminating a sample to thereby generate a plurality of first interacted photons selected from the group consisting of: photons absorbed by the sample, photons reflected by the sample, photons emitted by the sample, photons scattered by the sample, and combinations thereof in step 301. The sample may be any object including but not limited to: a human hand, a passport, a credit card, a driver's license, a boarding pass, a human body part, a piece of human clothing, a human-wearable item, a shoe, an airline ticket, and combinations thereof. In one embodiment, the sample may be illuminating using a passive illumination source, such as the sun. In another embodiment, the sample may be illuminated using an active illumination source. In one embodiment, the active illumination source is an active broadband illumination source. In one embodiment, a tungsten white light illumination source can be used as an active illumination source.

In step 302, the plurality of first interacted photons is assessed using a visible imaging device, wherein said assessing comprises obtaining a visible data set to thereby identify an area of interest in the sample. In step 303, the visible data set is analyzed to thereby identify an area of interest in the sample. In one embodiment, analyzing of said visible data set further comprises searching a visible database in accordance with the visible data set in order to identify a known visible data set from said visible database, wherein said visible database contains a plurality of known visible data sets, and wherein each known visible data set is associated with one or more of the following: an explosive compound, a formulation additive of an explosive material, a binder of an explosive material, a residue of an explosive material, and combinations thereof. In one embodiment, the searching may comprise searching for attributes such as size, shape, color, and morphology. In another embodiment, the visible data set may be assessed by visual inspection by a user. Such assessment may comprise a user analyzing the visible data set for size, shape, color and morphology. In one embodiment, the visible data set comprises a visible image representative of said sample. In one embodiment, the visible image may comprise at least one of a RGB image, a series of streaming RGB images, and a RGB video image.

The area of interest is illuminated in step 304 to thereby generate a plurality of second interacted photons selected from the group consisting of: photons absorbed by the sample, photons reflected by the sample, photons emitted by the sample, photons scattered by the sample, and combinations thereof. In step 305 the second interacted photons are assessed using a spectroscopic imaging device, wherein said assessing comprises obtaining a SWIR data set representative of said area of interest of said sample. A SWIR database is searched in accordance with the SWIR data set in step 306 in order to identify a known SWIR data set from said SWIR database, wherein said SWIR database contains a plurality of known SWIR data sets, and wherein each known SWIR data set is associated with a known explosive compound. In one embodiment, searching of at least one of the visible database and the SWIR database comprises applying a similarity metric. Such application may comprise generating a score representative of the likelihood of a match between the sample and the known SWIR data set. In one embodiment, this similarity metric may comprise a multivariate analysis method. The similarity metric applied may be any known in the art including but not limited to: a Euclidean distance metric, a spectral angle mapper metric, a spectral information divergence metric, a Mahalanobis distance metric, a spectral unmixing algorithm, principle component analysis, partial least squares regression, spectral mixture resolution, cosine correlation analysis, multivariate curve resolution, and combinations thereof.

In one embodiment, the plurality of SWIR data sets includes at least one of: a plurality of SWIR spectra corresponding to the known explosive compounds and a plurality of spatially accurate wavelength resolved SWIR spectroscopic images corresponding to the known explosive compounds. The explosive compound may comprise, but is not limited to: nitrocellulose, nitroglycerin, 1,3,5-trinitroperhydro-1,3,5-triazine ("RDX"), 1,3,5,7-tetranitroperhydor-1,3,5,7-tetrazocine ("HMX"), 1,3,-dinitrato-2,2-bis (nitratomethyl) propane ("PETN"), Ammonium Nitrate, and combinations thereof. An explosive compound in the area of interest is identified in step 307 based on the known SWIR data set identified by said searching.

In one embodiment, the method further comprises passing at least one of the plurality of first interacted photons and the second interacted photons through a filter. The filter may comprise a tunable filter selected form the group consisting of: a Multi-Conjugate Tunable Filter ("MCF"), a Liquid Crystal Tunable Filter ("LCTF"), Fabry Perot angle tuned filter, acousto-optic tunable filter, a Lyot filter, an Evan split element liquid crystal tunable filter, a Sole liquid crystal tunable filter, a spectral diversity filter, a photonic crystal tunable filter, a fixed wavelength Fabry Perot tunable filter, an air-tuned Fabry Perot tunable filter, and combinations thereof.

In one embodiment, the system and method of the present disclosure utilizes ChemImage Multi-Conjugate Filter technology available from ChemImage Corporation, Pittsburgh, Pa. This technology is more fully described in U.S. Pat. No. 7,362,489, entitled "Multi-Conjugate Liquid Crystal Tunable Filter" and U.S. Pat. No. 6,992,809, also entitled "Multi-Conjugate Liquid Crystal Tunable Filter." Both of these patents are hereby incorporated by reference in their entireties.

In one embodiment, the tunable filter sequentially passes photons absorbed, reflected, emitted, and/or scattered by the sample into a plurality of predetermined wavelength bands. The plurality of predetermined wavelength bands may include specific wavelengths or ranges of wavelengths. In one embodiment, the predetermined wavelength bands include specific wavelengths characteristic of the sample undergoing analysis. The wavelengths that can be passed may range from 200 nm (ultraviolet) to 2000 nm (far infrared). The choice of tunable filter depends on the desired optical region and/or the nature of the sample being analyzed.

In one embodiment, the method may be configured to operate in a proximate, standoff, or On-the-Move configuration ("OTM"). In another embodiment, the system and method may be configured to enable integration with LWIR. MM wave, and/or GPR sensors via industry standard fusion software. In another embodiment, the system and method may be configured to enable integration with other spectroscopic modalities. In one embodiment, this fusion software may comprise ChemImage Corporation's (Pittsburgh, Pa.) Forensic Integrated Search Technology ("FIST"). This technology is more fully described in pending U.S. patent application Ser. No. 11/450,138, filed on Jun. 9, 2006, entitled "Forensic Integrated Search Technology"; Ser. No. 12/017,445, filed on Jan. 22, 2008, entitled "Forensic Integrated Search Technology with Instrument Weight Factor Determination"; Ser. No. 12/196,921, filed on Aug. 22, 2008, entitled "Adaptive Method for Outlier Detection and Spectral Library Augmentation"; and Ser. No. 12/339,805, filed on Dec. 19, 2008, entitled "Detection of Pathogenic Microorganisms Using Fused Sensor Data". Each of these applications are hereby incorporated by reference in their entireties. Pending patent applications related to this technology also include: 61/335,785, 61/301,814, hereby incorporated by reference in their entireties.

Figure 4:
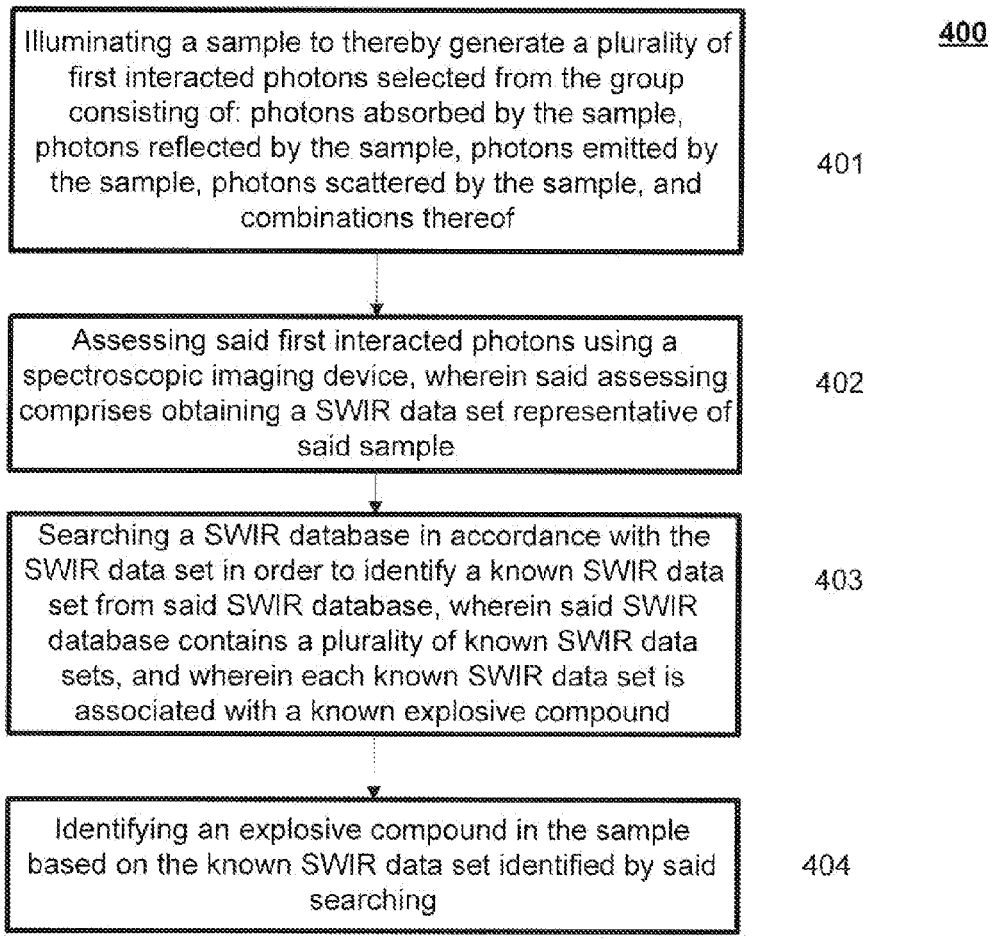
FIG. 4 is representative of a method of the present disclosure.

Another embodiment is represented by FIG. 4. The method 400 provides for illuminating a sample in step 401 to thereby generate a plurality of first interacted photons selected from the group consisting of: photons absorbed by the sample, photons reflected by the sample, photons emitted by the sample, photons scattered by the sample, and combinations thereof. The sample may be any object including but not limited to: a human hand, a passport, a credit card, a driver's license, a boarding pass, a human body part, a piece of human clothing, a human-wearable item, a shoe, an airline ticket, and combinations thereof. In step 402 said first interacted photons are assessed using a spectroscopic imaging device, wherein said assessing comprises obtaining a SWIR data set representative of said sample. In step 403 a SWIR database is searched in accordance with the SWIR data set in order to identify a known SWIR data set from said SWIR database, wherein said SWIR database contains a plurality of known SWIR data sets, and wherein each known SWIR data set is associated with a known explosive material. In one embodiment, the plurality of known SWIR data sets includes at least one of: a plurality of SWIR spectra corresponding to the known explosive compounds and a plurality of spatially accurate wavelength resolved SWIR spectroscopic images corresponding to the known explosive compounds. An explosive compound in the sample is identified in step 404 based on the SWIR data set identified by said searching. The explosive compound may comprise, but is not limited to: nitrocellulose, nitroglycerin, 1,3,5-trinitroperhydro-1,3,5-triazine ("RDX"), 1,3,5,7-tetranitroperhydor-1,3,5,7-tetrazocine ("HMX"), 1,3,-dinitrato-2,2-bis (nitratomethyl) propane ("PETN"), Ammonium Nitrate, and combinations thereof.

Figure 5:
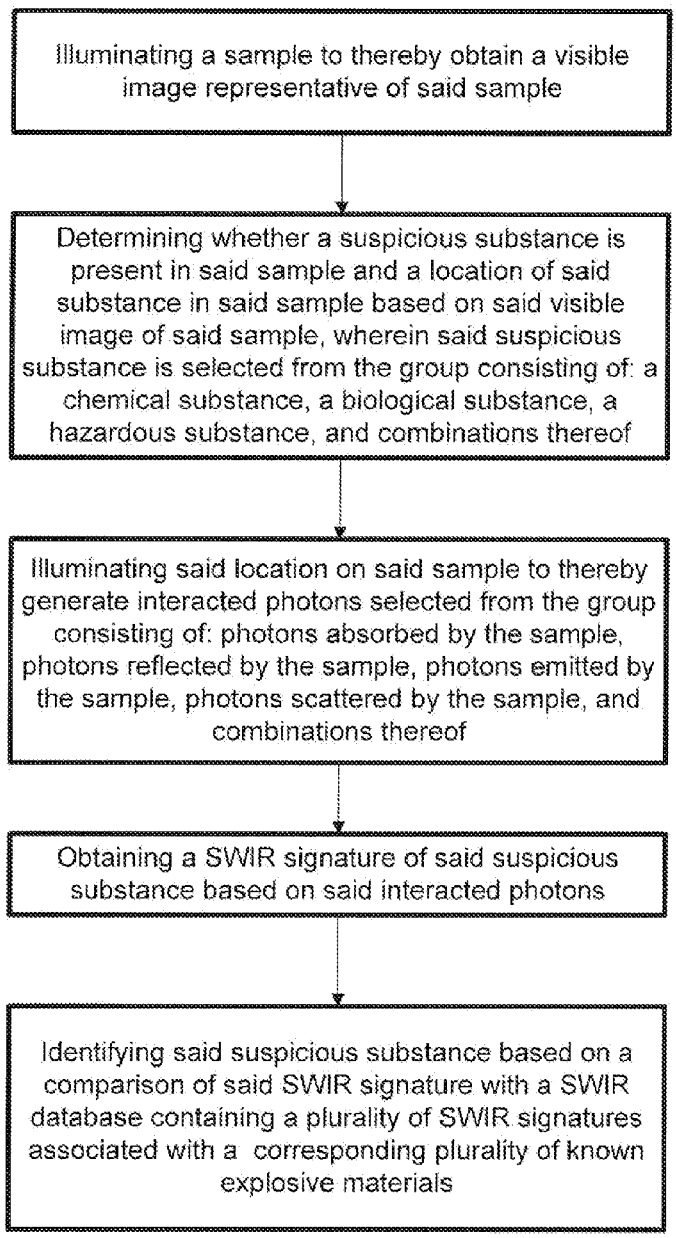
FIG. 5 is representative of a method of the present disclosure.

Another embodiment of the present disclosure is represented by FIG. 5. The method 500 provides for illuminating a sample in step 501 to thereby obtain a visible image representative of said sample. In step 502 whether a suspicious substance is present in the sample and a location of said substance in said sample is determined based on analyzing said visible image of said sample. wherein said suspicious substance is selected from the group consisting of: a chemical substance, a biological substance, a hazardous substance, and combinations thereof. Said location on said sample is illuminated in step 503 to thereby generate interactive photons selected from the group consisting of: photons absorbed by the sample, photons reflected by the sample, photons emitted by the sample, photons scattered by the sample. and combinations thereof. In step 504 a SWIR signature of said suspicious substance based on said interacted photons is obtained. Said suspicious substance is identified in step 505 based on a comparison of said SWIR signature with a SWIR database containing a plurality of SWIR signatures associated with a corresponding plurality of known explosive materials.

In another embodiment, the present disclosure provides for a storage medium containing machine readable program code, which when executed by a processor, causes the processor to perform a series of steps. In one embodiment, the processor can perform the steps outlined in FIGS. 4, 5, and/or 6.

Figure 6:
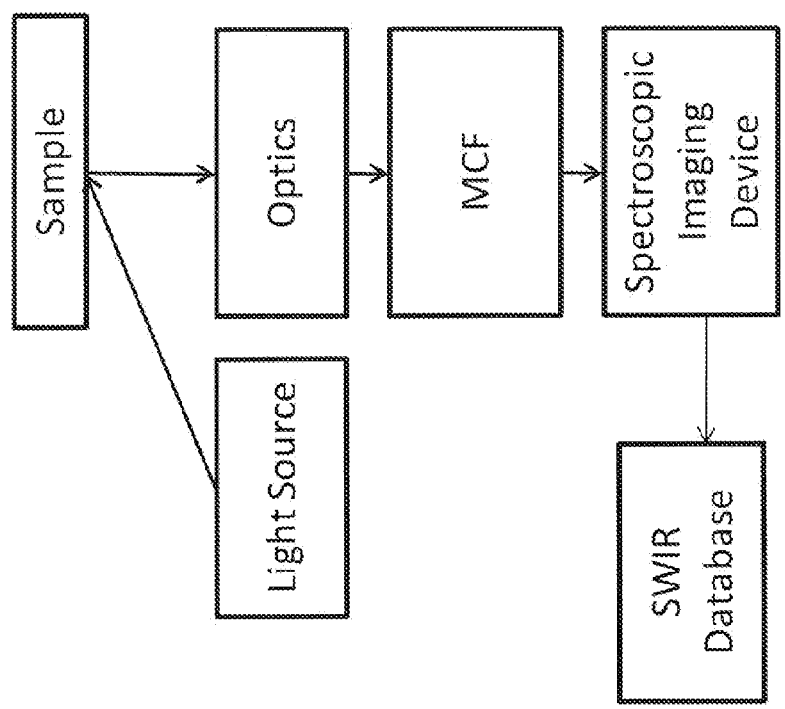
FIG. 6 illustrates a system of the present disclosure.

FIG. 6 is representative of a system of the present disclosure. In one embodiment, the system comprises an illumination source, optics, a MCF, a spectroscopic imaging device and a SWIR database which are used to detect explosive material on or in a sample. In another embodiment, the system may further comprise at least one of: a visible imaging device and a visible database.

Figures 7A, 7B, 7C:
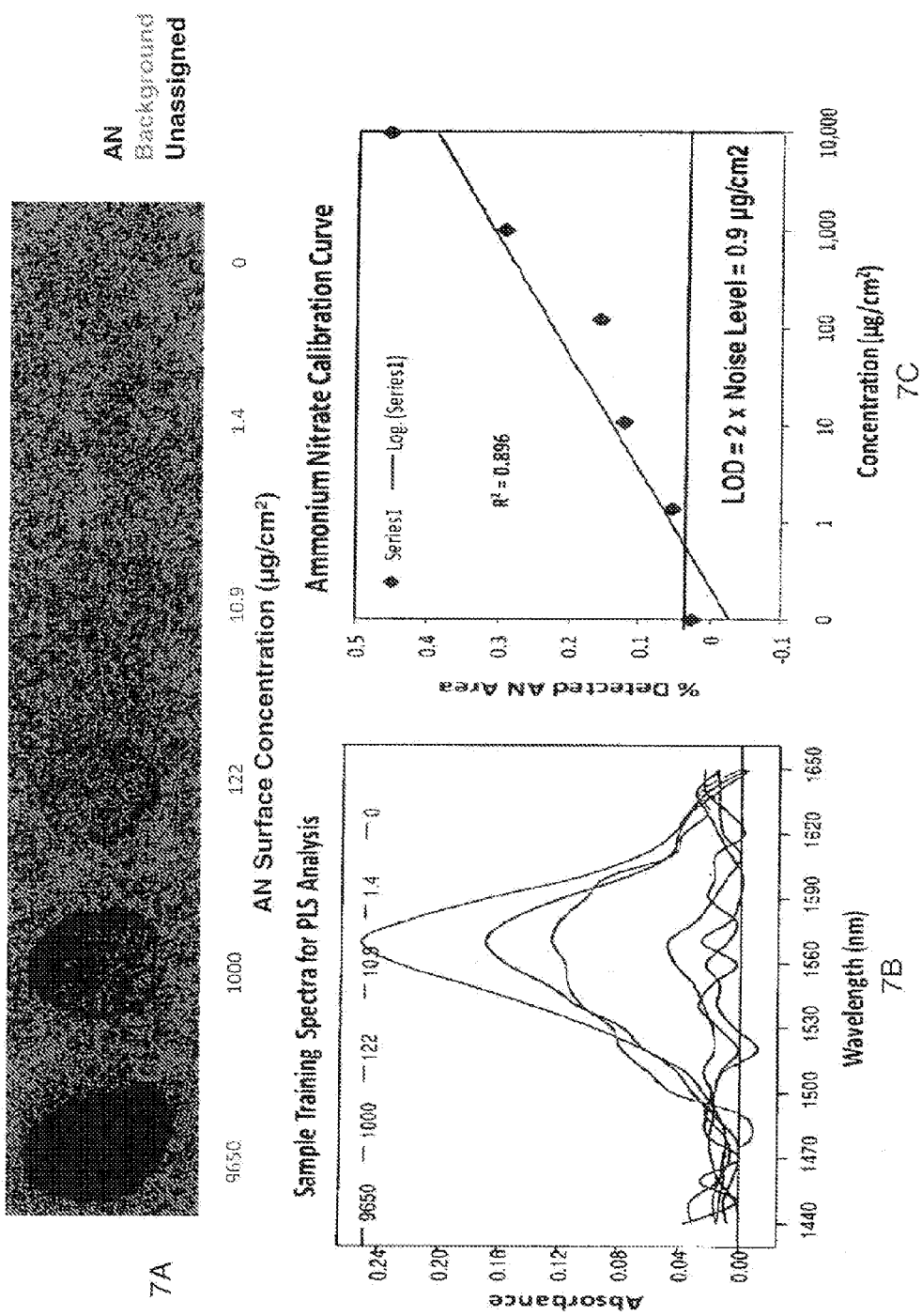
FIG. 7 illustrates the SWIR HSI sensor method limit of detection.

FIGS. 7A-7C illustrate of the limit of detection (LOD) study for Ammonium Nitrate (AN). FIG. 7A represents the detection images associated with each of the samples prepared for use in the study. The darker pixels correspond to locations where AN has been deposited when evaluated using a partial least squares (PLS) discriminant algorithm. FIG. 7B represents. the SWIR spectra associated with varying concentrations of AN on aluminum. FIG. 7C represents a calibration curve plotting % detected AN area v. log AN concentration indicates that the LOD for an AN on aluminum at 30 m standoff range is 0.9 µg/cm$^3$.

Figure 8:
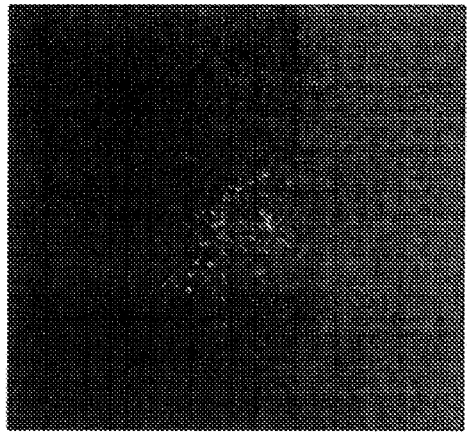
FIG. 8 illustrates the detection of Ammonium Nitrate on the surface of a leather shoe at 50 m distance.
Figure 8:
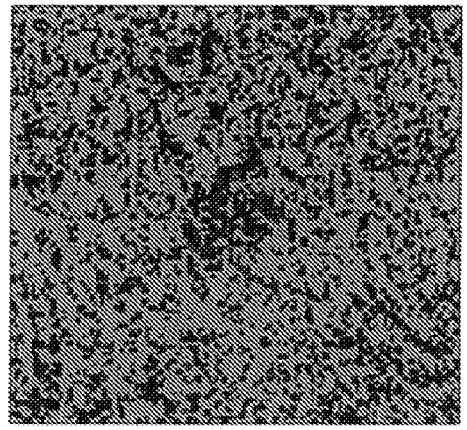
Figure 8:
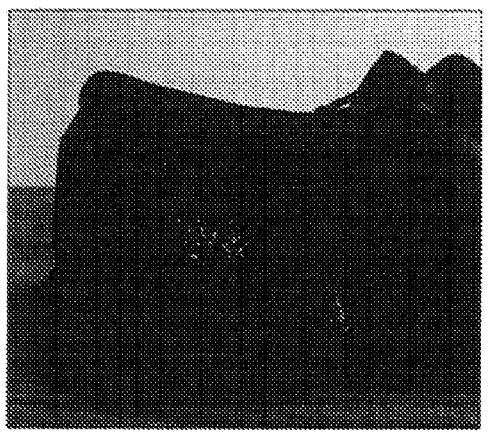
Figure 8:
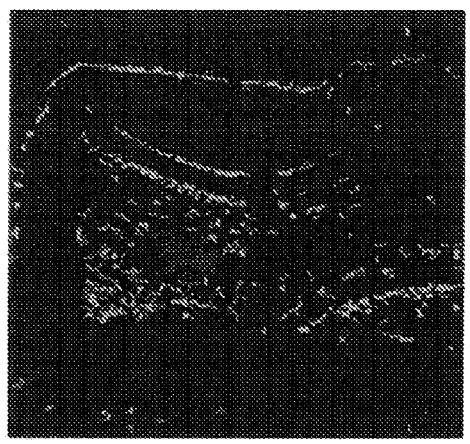

FIG. 8 illustrates the detection of Ammonium Nitrate (AN) residue on the surface of a leather shoe at 50 m standoff range.

Figure 9:
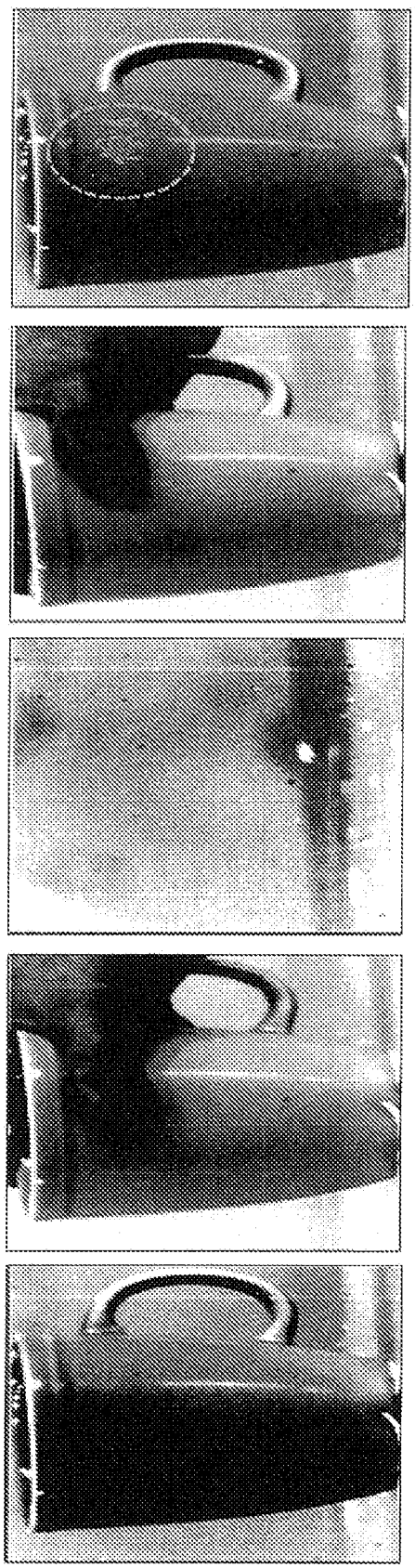
FIG. 9 illustrates the detection of Ammonium Nitrate explosive material as it is deposited on the surface of a coffee cup at 30 m distance.
Figure 10:
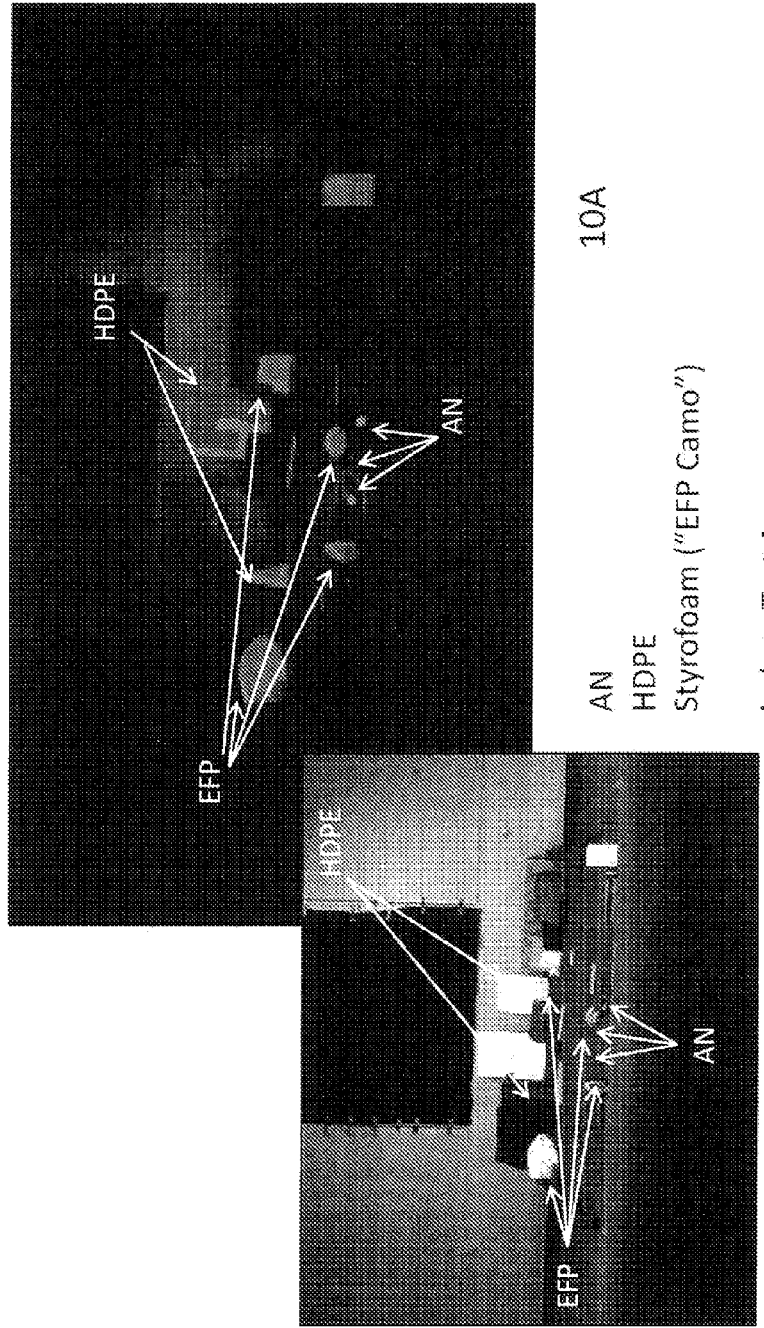
FIG. 10 illustrates moving the sensor from 40 meters to 10 meters and detecting AN On-the-Move.

FIG. 9 illustrates the detection of. Ammonium Nitrate (AN) explosive material as it is deposited on the surface of a coffee cup at 30 meters range. This is illustrative of the potential of the system and method of the present disclosure for detecting explosive materials on items that a passenger of interest may have come in contact with at a standoff distance. This is valuable because it enables the possibility of scanning other areas of a transportation station, that are within the standoff range of the sensor, in addition to a security checkpoint. These other areas may include a waiting area, restaurant, ticket counter, and baggage claim. Therefore, it is possible to detect explosive material on items that may be left outside of the security checkpoint by a passenger, increasing the likelihood that the material is detected. FIG. 10 illustrates moving the sensor from 40 meters to 10 meters and detecting AN On-the-Move. Multispectral data was collected from a standoff distance of 40 meters moving to 10 meters. In one embodiment, step scan data collection mythologies can be used. In one embodiment, the data is processed offline. FIG. 10A represents a RGB/optical overlay OTM image. FIG. 10B represents the indoor test area.

What is claimed is:
1. A method comprising:
   illuminating a sample to thereby generate a plurality of first interacted photons selected from the group consisting of: photons absorbed by the sample, photons reflected by the sample, photons emitted by the sample, photons scattered by the sample, and combinations thereof;
   assessing said plurality of first interacted photons using a visible imaging device, wherein said assessing comprises obtaining a visible data set representative of said sample;
   analyzing said visible data set to thereby identify an area of interest in the sample;
   illuminating said area of interest to thereby generate a plurality of second interacted photons selected from the group consisting of: photons absorbed by the sample, photons reflected by the sample, photons emitted by the sample, photons scattered by the sample, and combinations thereof;
   assessing said plurality of second interacted photons using a spectroscopic imaging device, wherein said assessing comprises obtaining a SWIR data set representative of said area of interest of said sample;
   searching a SWIR database in accordance with the SWIR data set in order to identify a known SWIR data set from said SWIR database, wherein said SWIR database contains a plurality of known SWIR data sets, and wherein each known SWIR data set is associated with a known explosive compound; and
   identifying an explosive compound in the area of interest based on the known SWIR data set identified by said searching.

2. The method of claim 1 further comprising passing at least one of said first plurality of photons and said second plurality of interacted photons through a multi-conjugate tunable filter.

3. The method of claim 1 further comprising passing at least one of said first plurality of interacted photons and said second plurality of interacted photons through a tunable filter selected from the group consisting of: a Fabry Perot angle tuned filter, an acousto-optic tunable filter, a liquid crystal tunable filter, a Lyot filter, an Evans split element liquid crystal tunable filter, a Sole liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter.

4. The method of claim 1 wherein said illuminating of at least one of said sample and said area of interest is performed at a standoff distance.

5. The method of claim 1 wherein said plurality of known SWIR data sets includes at least one of: a plurality of SWIR spectra corresponding to the known explosive compounds and a plurality of spatially accurate wavelength resolved SWIR spectroscopic images corresponding to the known explosive compounds.

6. The method of claim 1 wherein said sample includes at least one of: a human hand, a passport, a credit card, a driver's license, a boarding pass, a human body part, a piece of human clothing, a human-wearable item, a shoe, an airline ticket, and combinations thereof.

7. The method of claim 1 wherein said known explosive compound is selected from the group consisting of: nitrocellulose, nitroglycerin, 1,3,5-trinitroperhydro-1,3,5-triazine ("RDX"), 1,3,5,7-tetranitroperhydro-1,3,5,7-tetrazocine ("HMX"), 1,3-dinitrato-2,2-bis (nitratomethyl) propane ("PETN"), Ammonium Nitrate, and combinations thereof.

8. The method of claim 1 wherein said searching comprises applying a similarity metric that generates a score.

9. The method of claim 8 wherein said similarity metric is selected from the group consisting of: a Euclidean distance metric, a spectral angle mapper metric, a spectral information divergence metric, a Mahalanobis distance metric, a spectral unmixing algorithm, principle component analysis, partial least squares regression, spectral mixture resolution, cosine correlation analysis, multivariate curve resolution, and combinations thereof.

10. The method of claim 1 wherein said analyzing of said visible data set further comprises searching a visible database in accordance with the visible data set in order to identify a known visible data set from said visible database, wherein said visible database contains a plurality of known visible data sets, and wherein each known visible data set is associated with one or more of the following: an explosive compound, a formulation additive of an explosive material, a binder of an explosive material, a residue of an explosive material, and combinations thereof.

11. The method of claim 1 wherein said visible data set comprises a visible image representative of said sample.

12. The method of claim 1 wherein said visible data set comprises a RGB video image.

13. A method comprising: illuminating a sample to thereby obtain a visible image representative of said sample; determining whether a suspicious substance is present in said sample and a location of said substance in said sample based on said visible image of said sample, wherein said suspicious substance is selected from the group consisting of: a chemical substance, a biological substance, a hazardous substance, and combinations thereof; illuminating said location on said sample to thereby generate interacted photons selected form the group consisting of: photons absorbed by the sample, photons reflected by the sample, photons emitted by the sample, photons scattered by the sample, and combinations thereof; obtaining a SWIR signature of said suspicious substance based on said interacted photons; and identifying said suspicious substance based on a comparison of said SWIR signature with a SWIR database containing a plurality of SWIR signatures associated with a corresponding plurality of known explosive materials.

14. The method of claim 13 wherein said visible image comprises a RGB video image.

15. A system comprising:
a visible imaging device for assessing a sample to indentify an area of interest;
an illumination source to illuminate at least one of the sample and an area of interest in the sample to thereby generate a plurality of first interacted photons selected from the group consisting of: photons absorbed by the sample, photons reflected by the sample, photons emitted by the sample, photons scattered by the sample, and combinations thereof;
a tunable filter through which said interacted photons are passed, wherein said tunable filter is selected from the group consisting of: a multi-conjugate tunable filter, a Fabry Perot angle tuned filter, an acousto-optic tunable filter, a liquid crystal tunable filter, a Lyot filter, an Evans split element liquid crystal tunable filter, a Sole liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter;
a spectroscopic imaging device for assessing said interacted photons to thereby generate a SWIR data set representative of at least one of said sample and said area of interest in said sample; and
a SWIR database having plurality of known SWIR data sets, wherein each known SWIR data set is associated with one or more of the following: a known explosive compound, a formulation additive of explosive material, a binder of explosive material, and combinations thereof.

16. The system of claim 15 wherein said visible imaging device comprises a RGB video camera.

17. The method of claim 1 wherein at least one of said first plurality of interacted photons and said second plurality of interacted photons are collected using a telescope optic.

18. The system of claim 15 further comprising a telescope optic for collecting said plurality of interacted photons.

* * * * *